(12) United States Patent
Feltman

(10) Patent No.: US 11,547,657 B2
(45) Date of Patent: Jan. 10, 2023

(54) NATURAL SHAMPOO WITH BUCHU

(71) Applicant: Jo Ann Feltman, Temperance, MI (US)

(72) Inventor: Jo Ann Feltman, Temperance, MI (US)

( * ) Notice: Subject to any disclaimer, the term of this patent is extended or adjusted under 35 U.S.C. 154(b) by 100 days.

(21) Appl. No.: 17/169,339

(22) Filed: Feb. 5, 2021

(65) Prior Publication Data

US 2022/0249356 A1     Aug. 11, 2022

(51) Int. Cl.
| | | |
|---|---|---|
| *A61K 8/9789* | (2017.01) | |
| *A61K 8/67* | (2006.01) | |
| *A61K 8/73* | (2006.01) | |
| *A61K 8/92* | (2006.01) | |
| *A61K 8/9794* | (2017.01) | |
| *A61Q 5/02* | (2006.01) | |
| *A61K 8/06* | (2006.01) | |
| *A61K 8/44* | (2006.01) | |
| *A61K 8/96* | (2006.01) | |

(52) U.S. Cl.
CPC ............ *A61K 8/9789* (2017.08); *A61K 8/062* (2013.01); *A61K 8/44* (2013.01); *A61K 8/442* (2013.01); *A61K 8/673* (2013.01); *A61K 8/73* (2013.01); *A61K 8/922* (2013.01); *A61K 8/965* (2013.01); *A61K 8/9794* (2017.08); *A61Q 5/02* (2013.01); *A61K 2800/524* (2013.01); *A61K 2800/5922* (2013.01); *A61K 2800/805* (2013.01); *A61K 2800/85* (2013.01)

(58) Field of Classification Search
None
See application file for complete search history.

(56) References Cited

U.S. PATENT DOCUMENTS

| | | |
|---|---|---|
| 9,095,518 B2 | 8/2015 | Pressly |
| 2013/0344178 A1 | 12/2013 | Ko |
| 2016/0310397 A1 | 10/2016 | Johnson et al. |
| 2017/0012729 A1 | 1/2017 | Thomas et al. |

FOREIGN PATENT DOCUMENTS

| | | | |
|---|---|---|---|
| CN | 105287273 A | 2/2016 | |
| CN | 105496896 A | 4/2016 | |
| WO | WO-2008075207 A2 * | 6/2008 | ........... A61K 31/137 |

\* cited by examiner

*Primary Examiner* — Kyung S Chang

(57) ABSTRACT

A natural viscous liquid shampoo including a composition formulated with buchu extract and a preparation method thereof that would be harmless to the hair and scalp. The natural shampoo was created without sulphates and/or harmful chemicals and still cleanse your scalp but also balance your natural oils and promote healthier hair growth.

4 Claims, No Drawings

NATURAL SHAMPOO WITH BUCHU

FIELD OF INVENTION

The invention relates to the technical field of cosmetics and is a natural shampoo formulated with extracted buchu leaf (*Agathosma betulina*), which has antibacterial, anti-inflammatory and anti-microbial properties and also free of potentially harmful chemicals.

BACKGROUND OF INVENTION

The purpose of the instant application is to formulate a natural shampoo with the inclusion of buchu leaf, because the benefits of the buchu plant (*Agathosma betulina*) which has antibacterial, anti-inflammatory and anti-microbial properties. The buchu plant is indigenous to South Africa and is grown in the remote, dry mountainous regions of the Western Cape. The leaves have round oil glands found scattered across the leaf, which release an aromatic golden oil. The oil is said to have anti-inflammatory and anti-bacterial properties, that was perfect for this formulation and used along with Hyssop which is also an anti-microbial and anti-inflammatory and is used as a cleansing agent. These two base ingredients were exactly what the inventor was searching for to implement into natural shampoo.

Through research the inventor has realized that shampoos are made with sulphates, parabens and other harmful chemicals along with chemical compounds that are unidentifiable to the lay person and that are in most common shampoos that cause dryness to the hair and scalp which leads to irritation, frizz and hair loss. Because of these problems the inventor first thought to target the scalp with shampoos containing sulphates to create a nice thick lather that gives u a false sense of cleanliness, but there are fall backs to using sulphates because it is a detergent that strips natural oils from scalp, it can also cause hair to be dry, brittle and hair color to fade. Another potentially harmful chemical is parabens they are used in shampoos to prevent bacteria and as a preservative. But parabens can mimic the hormone estrogen and have been linked to increased growth of breast cancer cells, which makes them harmful. Discovering how these chemicals can be harmful the inventor wanted to invent a shampoo that not only cleaned the hair and scalp without stripping the natural oils but was also safe from harmful chemicals.

BRIEF SUMMARY OF INVENTOR

What the inventor has now found is scalp produces sebum from sebaceous glands that are grouped around follicles and if it isn't controlled properly user could end up with hyperactivity which causes flakiness that can lead to dandruff or more serious problems. The shampoo composition is comprised of natural surfactants that would remove sebum, dirt and skin debris from the hair and scalp without affecting the hair, scalp or health of the user. The primary surfactant coco betaine is included as an emulsifying agent to combine the oils and water-based ingredients. It is a medium-strength surfactant that comes from coconut oil and provides good foaming action, moisturizes and protects the hair and scalp. The secondary surfactant is called sodium lauroyl sarcosinate (SLS). SLS is a natural anionic surfactant used in many natural hair care products to provide a foam for gentle cleansing and increase body, suppleness and sheen. The most important part was to provide a natural surfactant that does not damage the hair and scalp. The pH of the total composition formula was tested at a 5.5, which is ideal for a healthy scalp.

There is a need for improvement of prior art and a method of making a natural shampoo that uses plant and herb extract with ingredients that are easily identified by the common man. The composition of said ingredients are seemingly different from commercial products, as it does not contain harmful chemicals, to name a couple, sulphates and parabens. The inventor wants to contrive a change and an improvement hereby incorporating the buchu and hyssop plant extracts along with ingredients that are safe and not harmful; and to create a natural shampoo that truly works at cleansing the scalp without stripping natural oils, thus leaving user with healthy shiny hair. The pH of the total composition formula was tested at a 5.5, which is ideal for a healthy scalp.

DETAILED DESCRIPTION OF THE INVENTION

The following list of ingredients were all added to the composition due to the benefits of each individual ingredient, nevertheless not to exclude any other possibilities.

Grapeseed oil, because when it comes to hair health, some claim that grapeseed oil can help restore hair's natural shine and vibrancy. Scalp naturally produces sebum, an oily substance, which keeps hair shiny and healthy. As people age, scalp's sebum production slows down, leading to dry scalp and brittle hair. The grapeseed oil moisturizes hair and stimulates hair growth.

Sunflower oil contains Vitamin E and is known to have benefits for hair health. They are both antioxidants and may help neutralize free radicals that can damage the hair and scalp. Sunflower oil also contains oleic acid, which can stop hair breakage and may make it seem like hair is growing faster (since the hair ends are not breaking off). Derived from the seeds of the sunflower the oil is high in essential fatty acids like phospholipids and ceramides. Ceramides keep the hair cuticle flat, helping to smooth hair, enhance shine and allow hair to endure wear and tear over time. They promote elasticity and moisture retention, and aid in strengthening hair, as well as antioxidants and vitamin E, making it deeply nourishing and soothing to dry hair and scalp. It locks in moisture and helps keeps hair healthy and strong.

Lemon contains citric acid and can address the root of hair problems by reducing oil and dandruff. This is especially true if users have a dry scalp or dandruff. The citric acid is also helpful due to its acidic properties to lower the pH of the formulation to promote a healthy scalp.

The sea salt or pink Himalayan salt is beneficial for hair growth. If users suffer from alopecia, or hair loss, it is recommended to use sea salt for natural stimulation of the growing of hair. Salt opens up blocked pores on the scalp thus allowing proper hair growth. Salt helps loosen and dissolve existing product build-up and dandruff as well as stimulates circulation for a healthy scalp. Pink salt also absorbs excess oil and moisture to prevent dandruff in the future.

Aloe vera contains proteolytic enzymes which repairs dead skin cells on the scalp. It also acts as a great conditioner and leaves hair smooth and shiny. It promotes hair growth, prevents itching on the scalp, reduces dandruff, conditions hair and balances pH.

Coconut oil promotes scalp health by fighting against such problems as dandruff. It moisturizes dry hair by adding luster, shine and softness to the hair and prevents hair breakage and split ends, contributing to hair length.

Xanthan gum a thickening agent 100% natural ingredient intent was chosen because of its entirely natural composition and used as a natural preservative. Peoples demand for a natural shampoo with a higher viscosity led me to include xanthan gum.

Biotin supplements have also been linked to hair growth since it assists in the production of keratin, the protein our hair is made of. Biotin promotes hair tensile strength; it is a non-toxic vitamin that has been reported safe and well-tolerated by the FDA. Especially when used on the scalp, a biotin shampoo can help increase body's levels of biotin, without having to take an oral supplement, and encourage healthy hair growth. Additional benefits are fuller healthier looking hair.

Natural preservatives such as, Leucidal SF Complete, used in combination of peptide technology with fermented radish root to deliver moisturizing and conditioning benefits as well as providing broad-spectrum activity to protect against bacteria, yeast, and mold in one product.

Distilled water is used as a vehicle for the beneficial oils extracted from the buchu and hyssop plant, that when steeped creates an oil mixed with water from the plants to use as a base for the natural shampoo.

The essential oils that are added to the composition are not only for scent but for added nutrients. The rosemary oil stimulates hair growth, preventing or slow progression of premature graying, dandruff and itchy scalp. Teatree oil-benefits are the same as rosemary but also help to balance scalps pH. Lemongrass oil promotes contraction of hair follicles, thereby preventing hair shedding with regular use. Peppermint oil increases the number of hair follicles, follicle depth, and overall hair growth. These essential oils are beneficial to the shampoo formulation because of the nutrients they themselves add to hair and scalp.

EMBODIMENT OF THE INVENTION

The first embodiment provides a natural buchu extract viscous liquid shampoo composition consisting of:
40-80% by weight distilled water, 0.2-10% buchu leaves, 0.2-10% hyssop leaves, 5-50% sodium lauroyl sarcocinate, 1-5% coconut oil, 1-10% pink himalayan salt, 0.4-4% apple cider vinegar, 2-10% aloe vera gel, 0.2-5% lemon juice, 1-5% sunflower oil, 1-5% grapeseed oil, 0.5-10% xanthan gum, 10-50% coco betaine, 1-10% biotin, 0.5-10% natural preservative comprised of peptides and fermented radish root and 0.2-2% essential oils.

The second embodiment provides a method of making a natural buchu extract viscous liquid shampoo composition consisting of a-j steps of:
a. providing a clean pot, adding to said pot 40-80% distilled water and 0.2-10% buchu leaves and 0.2-10% hyssop leaves;
b. under a heat means, steeping the buchu and hyssop leaves in said distilled water to provide a water-based extract
c. providing heat extracted buchu and hyssop water and adding 5-50% sodium lauroyl sarcosinate;
d. adding 1-5% coconut oil with stirring until melted and adding 1-10% pink himalayan salt;
e. preparing in a separate bowl 0.4-4% apple cider vinegar, 2-10% aloe vera gel and 0.2-5% lemon juice;
f. preparing in a separate bowl 1-5% sunflower oil, 1-5% grapeseed oil and 0.5-10% xanthan gum with stirring until blended;
g. mixing 10-50% coco betaine to prepared ingredients in step f) and combining them to allow stable emulsion between oil and water ingredients;
h. mixing and pouring combined ingredients of e), f) and g) with ingredients d) mixing with a hand mixer to emulsify the ingredients into a stable consistency of a viscous creamy liquid and allowing the ingredients to cool down to below 100 degrees;
i. combining 1-10% biotin and 0.5-10% natural preservative comprised of peptides and fermented radish root and adding to ingredients of h) and blending them for about 5 minutes;
j. while stirring adding 0.5-2% essential oils to the composition obtained from step i) to provide a liquid natural shampoo.

The third embodiment presents a hair composition consisting essentially of the natural buchu extract viscous liquid shampoo composition of the first embodiment.

The fourth embodiment presents a hair composition consisting essentially of the natural buchu extract viscous liquid shampoo obtained by the method of the second embodiment.

The invention claimed is:

1. A natural buchu extract viscous liquid shampoo composition consisting of:
40-80% by weight distilled water, 0.2-10% buchu leaves, 0.2-10% hyssop leaves, 5-50% sodium lauroyl sarcocinate, 1-5% coconut oil, 1-10% pink himalayan salt, 0.4-4% apple cider vinegar, 2-10% aloe vera gel, 0.2-5% lemon juice, 1-5% sunflower oil, 1-5% grapeseed oil, 0.5-10% xanthan gum, 10-50% coco betaine, 1-10% biotin, 0.5-10% natural preservative comprised of peptides and fermented radish root and 0.2-2% essential oils.

2. A method of making a natural buchu extract viscous liquid shampoo composition comprising a-j steps of:
a. providing a clean pot, adding to said pot 40-80% distilled water and 0.2-10% buchu leaves and 0.2-10% hyssop leaves;
b. under a heat means, steeping the buchu and hyssop leaves in said distilled water to provide a water-based extract;
c. providing heat extracted buchu and hyssop water and adding 5-50% sodium lauroyl sarcosinate;
d. adding 1-5% coconut oil with stirring until melted and adding 1-10% pink himalayan salt;
e. preparing in a separate bowl 0.4-4% apple cider vinegar, 2-10% aloe vera gel and 0.2-5% lemon juice;
f. preparing in a separate bowl 1-5% sunflower oil, 1-5% grapeseed oil and 0.5-10% xanthan gum with stirring until blended;
g. mixing 10-50% coco betaine to prepared ingredients in step f) and combining them to allow stable emulsion between oil and water ingredients;
h. mixing and pouring combined ingredients of e), f) and g) with ingredients d) with a hand mixer to emulsify the ingredients into a stable consistency of a viscous creamy liquid and allowing the ingredients to cool down to below 100 degrees;
i. combining 1-10% biotin and 0.5-10% natural preservative comprised of peptides and fermented radish root and adding to ingredients of h) and blending them for about 5 minutes; and j. while stirring adding 0.5-2% essential oils to the composition obtained from step i) to provide the liquid natural shampoo.

3. A hair composition consisting essentially of the natural buchu extract viscous liquid shampoo composition of claim 1.

4. A hair composition consisting essentially of the natural buchu extract viscous liquid shampoo obtained by the method of claim 2.

\* \* \* \* \*